United States Patent [19]

Muchowski et al.

[11] Patent Number: 5,082,950

[45] Date of Patent: Jan. 21, 1992

[54] PROCESS FOR PREPARING 5-AROYL-2,3-DIHYDRO-1H-PYRROLIZINE-1,1-DICARBOXYLATES (II) AND INTERMEDIATES THEREFOR

[75] Inventors: Joseph M. Muchowski, Sunnyvale; In-Seop Cho, Mountain View, both of Calif.

[73] Assignee: Syntex (U.S.A.) Inc., Palo Alto, Calif.

[21] Appl. No.: 596,802

[22] Filed: Oct. 12, 1990

[51] Int. Cl.$^5$ ................ C07D 487/04; C07D 207/337
[52] U.S. Cl. ..................... 548/453; 548/539
[58] Field of Search ................... 548/453, 539

[56] References Cited

U.S. PATENT DOCUMENTS

| | | | |
|---|---|---|---|
| 4,089,969 | 5/1978 | Muchowski et al. | 424/274 |
| 4,347,185 | 8/1982 | Muchowski et al. | 260/326.25 |
| 4,347,186 | 5/1982 | Muchowski et al. | 548/516 |
| 4,347,187 | 8/1982 | Muchowski et al. | 548/516 |
| 4,353,829 | 10/1982 | Thurber et al. | 260/326.25 |
| 4,873,340 | 10/1989 | Muchowski et al. | 548/453 |

OTHER PUBLICATIONS

A. Citterio et al., Tet. Lett., 30 (10), 1289–1292 (1989), "Oxidative Deprotonation of Carbonyl Compounds by Fe(III) Salts".

A. Citterio et al., J. Org. Chem., 54, 2713–2718 (1989), "Manganese (III) Acetate Induced Cyclization . . . ".

J. White et al., J. Org. Chem., 42(26), 4248–4251 (1977), "The Vilsmeier-Haack Aroylahon of Pyrrols Reexamined".

C. Gonzalez et al., Can. J. Chem., 61, 1697–1702 (1983), "Protecting Groups for the Pyrrole Nitrogen Atom . . . ".

E. I. Heiba et al., Org. Syn., 61, 22–24, "Substituted γ-Butyrolactones from Carboxylic Acids . . . ".

J. D. McClure, J. Org. Chem., 21, 2365–2368 (1962), "Synthesis of Spiroundecatrienones . . . ".

N. Kornblum et al., J. Am. Chem. Soc., 81, 4113–4114 (1959), "A New and Selective Method of Oxidation . . . ".

L. B. Levy, J. Org. Chem., 54, 253–254 (1989), "Facile Oxidation of Manganese (II) . . . ".

C. Walling, Accts. Chem. Res., 8, 125–131 (1975), "Fenton's Reagent Revisited".

H. C. Brown et al., Angew. Chem. Internat. Ed., 11(8), 692–700 (1972), "Organic Syntheses via Free-Radical Displacement Reactions . . . ".

Primary Examiner—David B. Springer
Attorney, Agent, or Firm—Derek P. Freyberg

[57] ABSTRACT

5-Aroyl-2,3-dihydro-1H-pyrrolizine-1,1-dicarboxylates of the formula

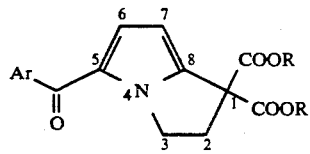

(I)

are prepared from 2-aroylpyrroles. Hydrolysis and mono-decarboxylation of these compounds affords ketorolac and related compounds.

18 Claims, No Drawings

PROCESS FOR PREPARING 5-AROYL-2,3-DIHYDRO-1H-PYRROLIZINE-1,1-DICARBOXYLATES (II) AND INTERMEDIATES THEREFOR

CROSS-REFERENCE TO RELATED APPLICATION

This application is related to the subject matter of our copending and commonly assigned U.S. Pat. application Ser. No. 07/596,843, filed Oct. 12, 1990, for "A Process for Preparing 5-Aroyl-2,3-Dihydro-1-H -Pyrrolizine-1,1 -Dicarboxylates (I)", which is incorporated herein by reference.

BACKGROUND OF THE INVENTION

1. Field of the Invention

This invention provides novel processes for preparing substituted pyrrolizine compounds. More particularly, this invention provides processes for the preparation of 5-aroyl-2,3-dihydro-1H-pyrrolizine-1,1-dicarboxylates (I)

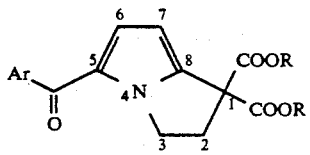

from 2-aroylpyrroles. Hydrolysis and mono-decarboxylation of compounds of formula I affords ketorolac and related compounds.

2. Background to the Invention

5-Aroyl-2,3-dihydro-1H-pyrrolizine-1-carboxylic acids (II), and the pharmacologically acceptable salts and esters thereof, are now under study

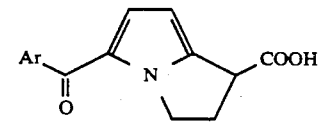

as analgesic, anti-inflammatory, and anti-pyretic agents for mammals, including man. They are also smooth muscle relaxants.

Two exemplary compounds under clinical study in man are ketorolac, 5-benzoyl-2,3-dihydro-1H-pyrrolizine-1-carboxylic acid, (II, $Ar=C_6H_5$) which is currently being marketed in the U.S., Italy, Holland, and New Zealand, and anirolac, 5-p-anisoyl-2,3-dihydro-1H-pyrrolizine-1-carboxylic acid, (II, $Ar=p-CH_3O-C_6H_5$), both disclosed in U.S. Pat. No. 4,089,969 (Muchowski et al., assigned to Syntex (U.S.A.) Inc.). Other compounds, where the 5-aroyl substituents are substituted or unsubstituted benzoyl, furoyl, thenoyl, and pyrroyl, and where the 6-and/or 7-position on the pyrrolizine nucleus is optionally substituted by lower alkyl or halogen, and uses thereof, are also disclosed in a series of patents assigned to Syntex (U.S.A.) Inc., beginning with U.S. Pat. No. 4,089,969, and including U.S. Pat. Nos. 4,087,539; 4,097,579; 4,140,698; 4,232,038; 4,344,943; 4,347,186; 4,458,081; 4,347,187; 4,454,326; 4,347,185; 4,505,927; 4,456,759; 4,353,829; 4,397,862; 4,457,941; and 4,454,151. U.S. Pat. Nos. 4,511,724 and 4,536,512, assigned to Merck & Co., Inc., disclose 5-(substituted pyrrol-2-oyl)-2,3-dihydro-1H-pyrrolizine-1-carboxylic acid derivatives and 5-(2,3-dihydro-1H-pyrrolizine-2-oyl)-2,3-dihydro-1H-pyrrolizine-1-carboxylic acid derivatives, respectively.

Various methods for the preparation of these pyrrolizines are exemplified in the patent and chemical literature.

For example, U.S. Pat. Nos. 4,347,186; 4,458,081; 4,347,187; and 4,454,326 disclose the preparation of 5-aroyl-pyrrolizines from pyrroles, and certain intermediates, by the following route:

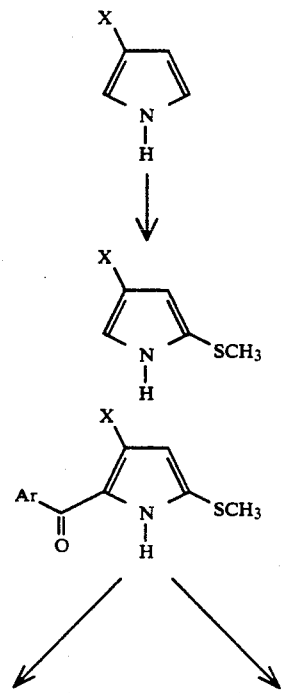

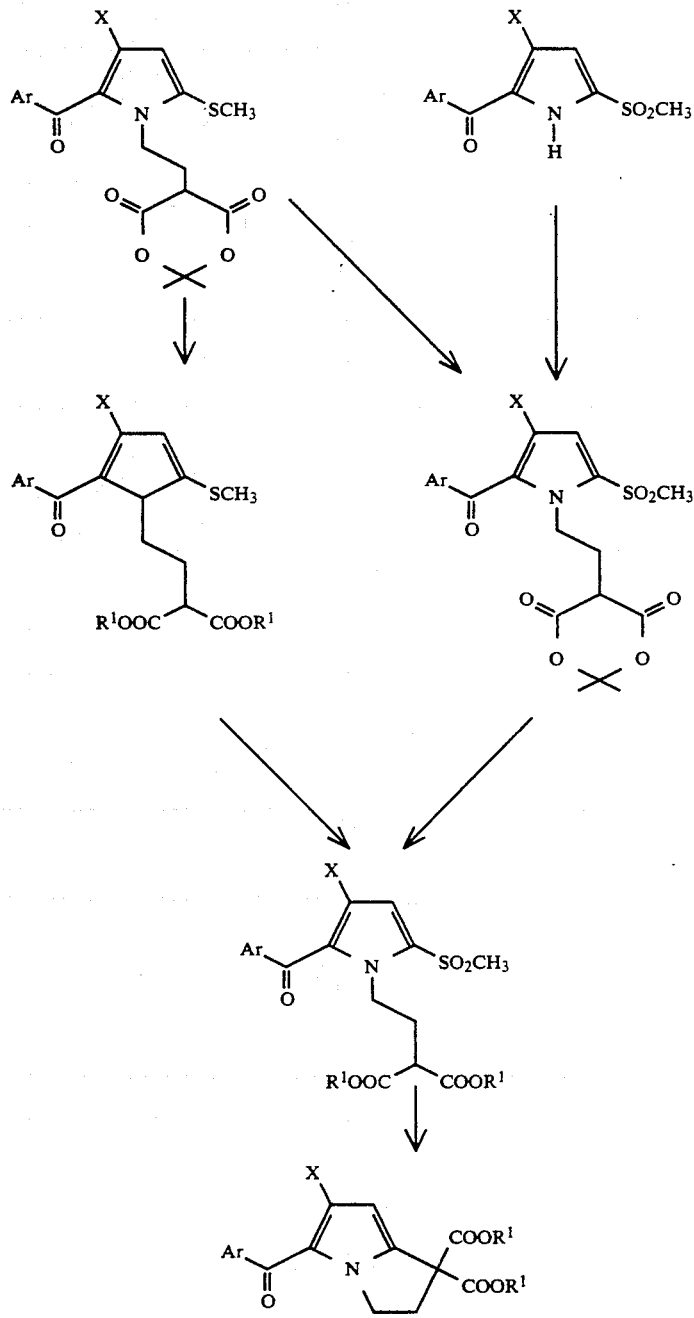

wherein:
R[1] and X are independently hydrogen or lower alkyl; and
Ar is a moiety selected from the group consisting of

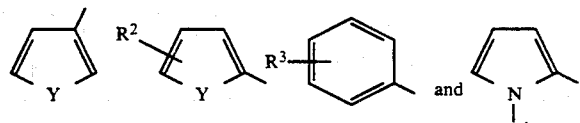

in which:
R[2] is hydrogen, methyl, chloro, or bromo, the R[2] substitution being at the 3-, 4- or 5-position of the ring;
R[3] is hydrogen, lower alkyl, lower alkoxycarbonyl, lower alkoxycarbonyl, lower alkylcarbonyl, fluoro, chloro or bromo, the R3 substitution being at any available position in the ring;
R[4] is hydrogen or lower alkyl; and
Y is oxygen or sulfur.

U.S. Pat. Nos. 4,347,185; 4,505,927; and 4,456,759 disclose the preparation of 5-aroyl-pyrrolizines from pyrroles, and certain intermediates, by the following route:

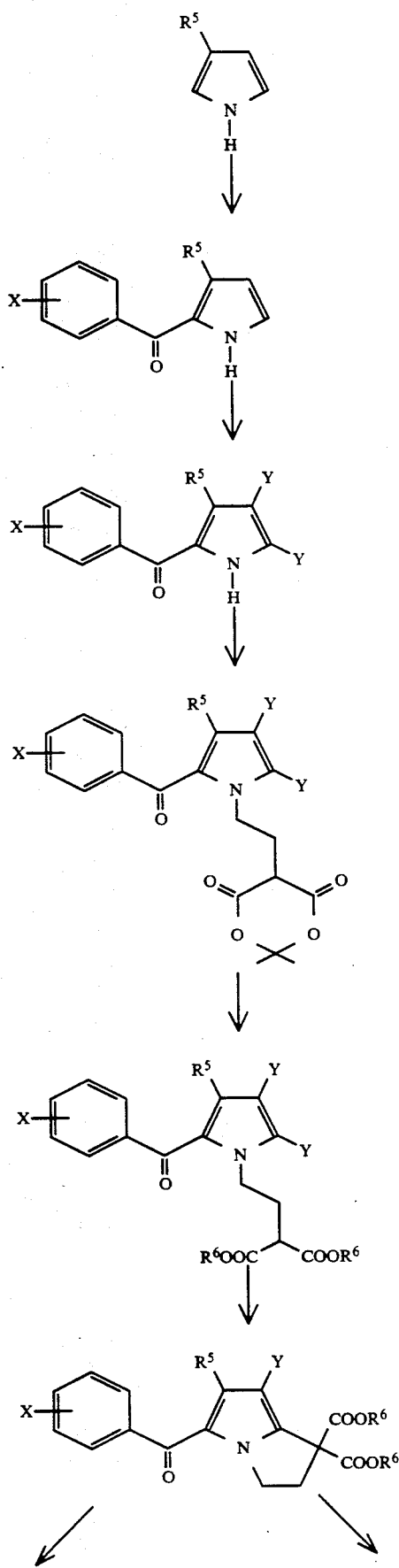

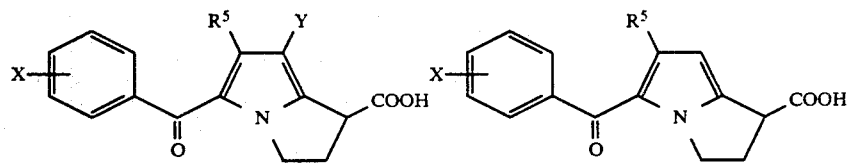

wherein:
R[5] is hydrogen or lower alkyl;
R[6] is lower alkyl:
X is hydrogen, lower alkyl, lower alkoxy, lower alkoxycarbonyl, carboxyl, lower alkylcarbonyl, sulfonic acid, sulfonic acid alkyl ester, fluoro, chloro, or bromo; and
Y is chloro or bromo.

U.S. Pat. No. 4,873,340, issued Oct. 10, 1989, discloses the preparation of 5-aroyl-2,3-dihydro-1H-pyrrolizine-1,1-dicarboxylates from 2-halopyrroles, and certain intermediates, by the following route:

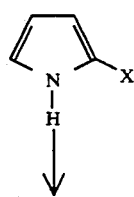

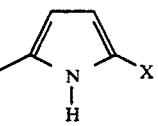

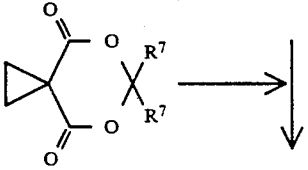

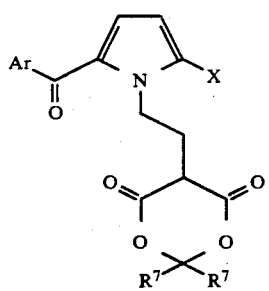

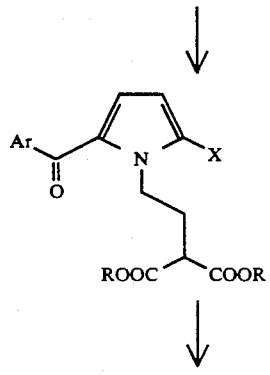

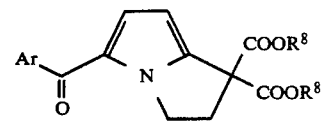

wherein
R[8] is lower alkyl;
Ar is an aryl group not containing hydrogen bonded to a pyrrole nitrogen; and
each R[7] is independently lower alkyl; and
X is bromo or chloro.

It has recently been reported that iron (III) salts and manganese (III) acetate can induce the oxidative radical cyclization of β-dicarbonyl moieties to form homocyclic aromatic systems. A. Citterio, et al., *Tetrahedron Letters*, 30, 1289 (1989); *J. Org. Chem.*, 54, 2713 (1989).

The disclosures of these patents and literature articles and other patents and articles referred to throughout this application are incorporated herein by reference.

SUMMARY OF THE INVENTION

In a first aspect, this invention provides a novel process for the preparation of 5-aroyl-2,3-dihydro-1H-pyrrolizine-1,1-dicarboxylates (I)

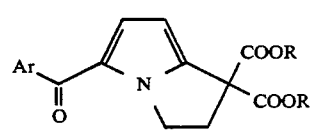 (I)

in which
R is lower alkyl; and
Ar is an aryl group, which does not contain nitrogen which is substituted with hydrogen; from 2-aroylpyrroles via radical addition followed by an intermolecular double alkylation.

The preparation may be represented schematically:

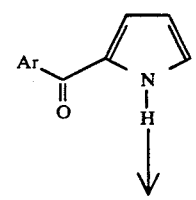

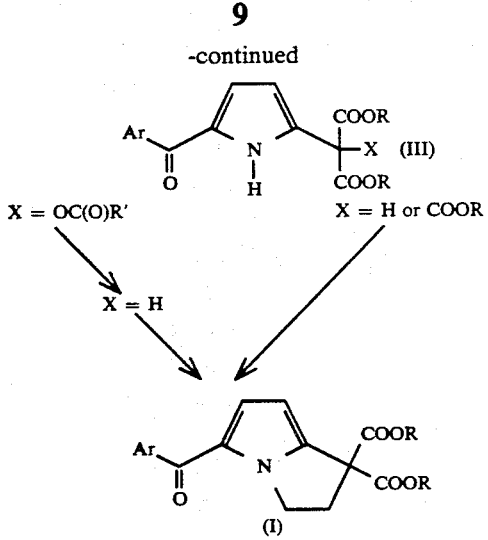

in which
R and Ar are as previously defined; and
X is selected from the group consisting of alkoxycarbonyl, acyloxy, and hydrogen.

In a second aspect, this invention provides for the preparation of 5-aroyl-2,3-dihydro-1H-pyrrolizine-1-carboxylic acids and their pharmaceutically acceptable salts by the preparation of compounds of formula I by the processes described above, followed by hydrolysis and decarboxylation thereof, optionally followed by salt formation.

In a third aspect, this invention provides for novel compounds of formula III, wherein R, Ar, and X are as described above, which is useful as an intermediate in the processes herein.

DETAILED DESCRIPTION OF THE INVENTION

Definitions and General Parameters

Unless otherwise stated, the following terms used in the specification and claims have the meanings given below:

"Alkyl", denoted generally by R, e.g., by $R^1$ or $R^2$, refers to straight or branched chain aliphatic groups having 1-2 carbon atoms, or aliphatic groups having 3-12 carbon atoms and containing at least one cyclic aliphatic group (cycloalkyl group). Those alkyl groups having 1-8 carbon atoms, and especially those having 1-4 carbon atoms, are presently preferred. The cycloalkyl groups having 3-8 carbon atoms are presently preferred. Alkyl groups include those exemplified by methyl, ethyl, cyclopropyl, cyclopropylmethyl, secbutyl, heptyl, and dodecyl. All of the above can either be unsubstituted or substituted with one or more non-interfering sustituents, e.g., halogen; $C_1-C_4$ alkoxy; $C_1-C_4$ acyloxy; formyl; alkylenedioxy; benzyloxy; phenyl or benzyl, each optionally substituted with from 1 to 3 substituents selected from halogen, $C_1-C_4$ alkoxy or $C_1-C_4$ acyloxy. The term "non-interfering" characterizes the substituents as not adversely affecting any reactions to be performed in accordance with the process of this invention. If more than one alkyl group is present in a given molecule, each may be independently selected from "alkyl" unless otherwise stated. Preferred alkyl groups are $C_1-C_4$ alkyl, and particularly preferred are methyl and ethyl.

"Lower alkyl" refers to an alkyl group of one to six carbon atoms. Lower alkyl groups include those exemplified by methyl, ethyl, n-propyl, i-propyl, n-butyl, t-butyl, i-butyl (2-methylpropyl), cyclopropylmethyl, i-amyl, n-amyl and hexyl. Preferred lower alkyls are methyl and ethyl. If more than one alkyl group is present in a given molecule, each may be independently selected from "lower alkyl" unless otherwise stated.

"Lower alkenyl" refers to a branched or unbranched singly ethylenically unsaturated hydrocarbon chain containing from two to six carbon atoms. Lower alkenyl groups include those exemplified by ethenyl (vinyl), propenyl, and butenyl.

"Lower alkynyl" refers to a branched or unbranched singly acetylenically unsaturated hydrocarbon chain containing from two to six carbon atoms. Lower alkynyl groups include those exemplified by ethynyl (acetylenyl), propynyl, and butynyl.

"Lower alkoxide", "lower alkanol", "lower alkylamine", "lower alkyl ester", "lower alkanoic acid", and similar terms refer to alkoxides, alkanols, alkylamines, alkyl esters, alkanoic acids, etc., in which the (or each) alkyl group is a "lower alkyl" as defined above.

"Alkyl radical" refers to an alkyl group which possesses at least one unpaired electron. Alkyl radicals include those exemplified by $CH_3\cdot$, $\cdot CH_2CH_3$, and the like.

"Aryl", denoted by Ar, includes monocyclic or condensed carbocyclic aromatic groups having from 6 to 20 carbon atoms. Aryl groups include those exemplified by phenyl and naphthyl. These groups may be substituted with one or more non-interfering substituents, e.g., those selected from lower alkyl; lower alkenyl; lower alkynyl; lower alkoxy; lower alkylthio; lower alkylsulfinyl; lower alkylsulfonyl, dialkylamine; halogen; hydroxy; phenyl; phenyloxy; benzyl; benzoyl; and nitro. Each substituent may be optionally substituted with additional non-interfering substituents. Preferred aryl groups include, for example, those selected from the group consisting of

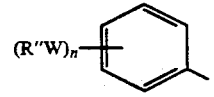

in which
R'' is hydrogen, fluoro, chloro, bromo or nitro, or lower alkyl, optionally substituted by halogen;
W is a covalent bond, -O-, -S-, -S(O)-, -S(O)$_2$-, -NR-, -CHR-, where R is alkyl; except that if R'' is nitro, fluoro, chloro, or bromo, then W is a covalent bond; and
n is 0 to 5;

A particularly preferred aryl group is selected from 4-(R''W)-phenyls, especially phenyl, 4-methoxy-phenyl, and 4-methylthiophenyl.

"Aroyl" refers to the group -C(O)-Ar, where Ar is an aryl group.

"Acyl" refers to the group -C(O)-R'', where R'' is lower alkyl.

"Acyloxy" refers to the group -OC(O)R'', where R'' is lower alkyl.

"Alkoxycarbonyl" refers to the group -C(O)OR'', where R'' is lower alkyl.

"Pharmaceutically acceptable salts" refer to those salts which retain the biological effectiveness and properties of the free acids and which are not biologically or otherwise undesirable, formed with alkali metal bases, such as sodium or potassium; alkaline earth metal bases such as calcium; and organic bases such as trometha- mine, diethylamine, ethanolamine, piperidine, isopropylamine, choline, caffeine, sodium hydroxide, and the like.

"Protic polar solvent" includes organic solvents such as methanol, ethanol, acetic acid, and the like.

"Aprotic polar solvent" includes organic solvents which may be either water-immiscible, such as halogenated hydrocarbons, e.g., methylene chloride, chloroform, and the like, or water-miscible, such as tetrahydrofuran, dimethoxyethane, dimethylformamide, dimethylsulfoxide, and the like.

"Nonpolar solvent" includes organic solvents such as benzene, toluene, carbon tetrachloride, and ligroin.

"Alkanoic acid" refers to compounds of the formula RCOOH where R is an alkyl group of one to ten carbons.

"Strong mineral acid" refers to an inorganic, water-soluble, easily dissociable Bronsted-Lowry acid, such as hydrochloric, sulfuric, phosphoric acids and the like.

"Strong base" refers to bases such as alkali metal hydroxides, alkali metal alkoxides, alkali metal hydrides, alkali metal di(lower alkyl)amines, and the like, for example, sodium hydroxide, potassium methoxide, sodium hydride, lithium di(isopropyl)amine, and the like.

"Weak base" refers to bases such as alkali metal acetates, alkali metal bicarbonates, tri(lower alkyl)amines, and the like, for example, sodium acetate, potassium bicarbonate, triethylamine, and the like.

"Strong mineral base" refers to an inorganic, water-soluble base with a pK$_b$ less than about 6, such as sodium hydroxide, sodium carbonate, potassium carbonate, and the like.

Isolation and purification of the compounds and intermediates described herein can be effected, if desired, by any suitable separation or purification procedure such as, for example, filtration, extraction, crystallization, column chromatography, thin-layer chromatography, thick-layer (preparative) chromatography, distillation, or a combination of these procedures. Specific illustrations of suitable separation and isolation procedures can be had by references to the examples hereinbelow. However, other equivalent separation or isolation procedures can, of course, also be used.

Compounds of formula I are named and numbered as illustrated below. For example, a compound of formula I where R is ethyl and Ar is phenyl

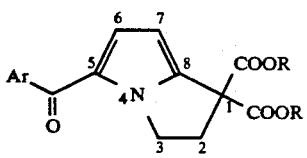

is named diethyl 5-benzoyl-2,3-dihydro-1H-pyrrolizine-1,1-dicarboxylate.

Synthesis of Compounds of Formula I

Compounds of formula I can be prepared as described in greater detail below and illustrated in Reaction Scheme I.

Preparation of 2-Aroylpyrroles

The 2-aroylpyrroles can be prepared by the procedure of White, et al., *J. Oro. Chem.*. 42, 4248 (1977) for the Vilsmeier-Haack aroylation of pyrroles utilizing aryl morpholide-acid chloride complexes or dialkylamine-acid chloride complexes. These reactions are further described in U.S. Pat. Nos. 4,353,829 (morpholides); and 4,089,969 and 4,347,186 (dialkylamides) for the preparation of aroyl pyrrolizines.

The aryl dialkylamides, aryl morpholides, aroyl halides, etc. are readily preparable by methods set forth in U.S. Pat. Nos. 4,353,829; 4,089,969; 4,347,186; 4,511,724; 4,533,671; and 4,536,512, all of which are incorporated herein by reference.

2-Aroylpyrroles may alternatively be prepared by the reaction of an aroyl halide and pyrrole.

Preparation of Compounds of Formula III where X is Alkoxycarbonyl using an Electrochemical Oxidant Compounds of formula III where X is alkoxycarbonyl may be produced via the reaction of an aroyl pyrrole with a trialkyl methanetricarboxylate and an electrochemical oxidant. "Electrochemical oxidant" refers to an agent providing to a reaction mixture an electrochemical potential exceeding 1 eV. The agent may either be an electrochemical cell containing the reaction mixture and having a voltage greater than 1 V between the electrodes; or may be a high valence metal ion, typically a transition metal ion in a higher oxidation state, having a redox potential greater than 1 eV. Examples of suitable high valence metal ions are Mn(III), e.g., as manganese(III) acetate, and Fe(III, e.g., as iron(III) perchlorate as described in the articles cited in the Background to the Invention. The high valence metal ion may be either added directly or generated in situ.

In a preferred embodiment, the high valence metal ion is a manganese(III) salt, preferably manganese(III) acetate. The manganese(III) salt may be added directly as manganese(III) acetate dihydrate or may be generated in situ from manganese(II). The procedure of Heiba, et al., *Org. Syn.*, 61, 22 (1983), wherein manganese(II) acetate tetrahydrate is oxidized with potassium permanganate, may be used to generate the manganese(III). An alternative procedure for generating manganese(III) involves a double redox cycle with manganese(II) acetate tetrahydrate, silver nitrate, and sodium persulfate. Additional procedures for producing high valence ions, and preferably manganese(III), in situ may also be used.

To a warm, preferably 60–80° C., mixture of a high valence metal ion, preferably a manganese(III) salt, and more preferably manganese(III) acetate, in an alkanoic acid, preferably acetic acid, or a polar aprotic solvent such as acetonitrile, is added a weak base, preferably sodium acetate, an aroyl pyrrole, preferably 2-benzoylpyrrole, and a trialkyl methanetricarboxylate, preferably triethyl methane tricarboxylate. The reaction mixture is stirred, preferably at 60° C., until the reaction is complete. The mixture is poured into water and extracted with a nonpolar solvent such as toluene. The solution is then concentrated under reduced pressure. The product, a compound of formula III where X is alkoxycarbonyl, preferably triethyl (5-benzoylpyrrol-2-yl)methane-tricarboxylate, may be isolated by conventional means.

Preparation of Compounds of Formula III where X is Acyloxy

Compounds of formula III where X is acyloxy may be produced via two alternative routes. An aroyl pyrrole and a dialkyl malonate may be reacted with an electrochemical oxidant, preferably a high valence metal ion, in an alkanoic acid solvent, preferably acetic acid. Alternatively, an aroyl pyrrole and a dialkyl halomalonate may be reacted with an electrochemical oxidant, preferably a high valence metal ion, in an alkanoic acid solvent, preferably acetic acid. In a preferred embodiment for either reaction, the high valence metal ion is a manganese(III) salt, preferably manganese(III) acetate. The manganese(III) salt may be added directly as manganese(III) acetate dihydrate or may be generated in situ as described above.

To a mixture of an aroyl pyrrole, preferably 2-benzoyl-pyrrole; and either, a dialkyl malonate, preferably diethyl malonate, or a dialkyl halomalonate, preferably diethyl bromomalonate, in an alkanoic acid, preferably acetic acid, or a aprotic polar solvent such as acetonitrile, is added a high valence metal ion, preferably a manganese(III) salt, and more preferably manganese(III) acetate dihydrate. The high valence metal ion may be either added directly or generated in situ. The reaction is stirred under a nitrogen atmosphere, preferably at 70-80° C. A weak base, preferably sodium acetate, may optionally be added. The reaction mixture is diluted with a aprotic polar solvent, such as diethyl ether, and filtered. The filtrate is washed with aqueous base and saturated aqueous sodium chloride, dried and concentrated under reduced pressure to yield a compound of formula III where X is acyloxy, preferably diethyl (5-benzoyl-pyrrol-2-yl) acetoxymethanedicarboxylate, which may be isolated by conventional means.

Preparation of Compounds of Formula III where X is Hydrogen

Compounds of formula III where X is hydrogen may be produced via the reaction of an aroyl pyrrole with a dialkyl halomalonate and an alkyl radical. A preferred alkyl radical, the methyl radical, is generated from the reaction of ferrous sulfate and hydrogen peroxide in dimethyl sulfoxide. In an alternative preferred embodiment, the alkyl radical is derived from a trialkylborane and oxygen in an aprotic solvent.

To a mixture of an aroyl pyrrole, preferably 2-benzoylpyrrole, and a dialkyl halomalonate, preferably diethyl bromomalonate, in a suitable solvent, is added an alkyl radical. A preferred alkyl radical, the methyl radical, may be generated from the reaction of ferrous sulfate and hydrogen peroxide in dimethyl sulfoxide. Alkyl radicals may also be generated from a trialkylborane, preferably triethylborane, with oxygen (air) in a nonpolar solvent. The reaction mixture is allowed to stir until the reaction is complete. The reaction mixture is poured into water and extracted with a aprotic polar solvent, such as methylene chloride or diethyl ether. The combined organic extracts are washed, dried, and concentrated under reduced pressure to yield a compound of formula III where X is hydrogen, preferably diethyl (5-benzoyl-pyrrol-2-yl) methanedicarboxylate, which may be isolated by conventional means.

Alternative Preparation of Compounds of Formula III where X is Hydrogen

An alternative preparation of compounds of formula III where X is hydrogen involves the reaction of a compound of formula III where X is acyloxy with a trialkylsilane and trifluoroacetic acid.

To a solution of a compound of formula III where X is acyloxy, preferably diethyl (5-benzoylpyrrol-2-yl)-acetoxymethanedicarboxylate, and a trialkylsilane, preferably triethylsilane, in a aprotic polar solvent, such as methylene chloride, is added trifluoroacetic acid. The reaction mixture is stirred, preferably at 40° C. Additional trialkylsilane and trifluoroacetic acid may be added during the course of the reaction. The mixture is cooled to room temperature, washed with cold dilute base and saturated aqueous sodium chloride, dried, and concentrated under reduced pressure. The residue may be purified by conventional means to produce a compound of formula III where X is hydrogen, preferably diethyl (5-benzoylpyrrol-2-yl)methane-dicarboxylate.

Preparation of Compounds of Formula I

A mixture of a compound of formula III where X is alkoxycarbonyl or hydrogen, preferably triethyl (5-benzoylpyrrol-2-yl) methanetricarboxylate or diethyl (5-benzoylpyrrol-2-yl) methanedicarboxylate; bromide or iodide ion, preferably tetrabutylammonium bromide; and a base, preferably potassium carbonate, in a 1,2-dihaloalkane, preferably 1, 2-dichloroethane is refluxed until the compound of formula III is consumed, preferably 1-2 days. The mixture is cooled and filtered. The filtrate is washed with a aprotic polar solvent, such as methylene chloride. The wash solution and the filtrate are combined and concentrated under reduced pressure. The residue is dissolved in a aprotic polar solvent, such as diethyl ether, washed, dried, and concentrated. The product, a compound of formula I, preferably 5-benzoyl-2,3-dihydro-1-H-pyrrolizine-1,1-dicarboxylate, may be isolated by conventional means.

Preparation of Compounds of Formula II

A compound of formula I may then be converted to the corresponding compound of formula II by the methods described in U.S. Pat. No. 4,347,186, which consist of treatment with base to accelerate ester hydrolysis, followed by treatment with acid to effect monodecarboxylation.

Preparation of Salts of Compounds of Formula II

The salts of the carboxylic acids of compounds of formula II, in particular the tromethamine salts of these acids, may be prepared by conventional methods, such as those disclosed in U.S. Pat. No. 4,089,969.

Preferred Processes

A preferred process involves the preparation of compounds of formula I via a radical addition to an aroyl pyrrole followed by an intermolecular double alkylation.

Preferred Compounds

The preferred compounds are compounds of formula III where X is alkoxycarbonyl, preferably triethyl (5-benzoylpyrrol-2-yl) methanetricarboxylate; compounds of formula III where X is acyloxy, preferably, diethyl (5-benzoylpyrrol-2-yl)acetoxymethanedicarboxylate; and compounds of formula III where X is hydrogen, preferably, diethyl (5-benzoylpyrrol-2-yl)methanedicarboxylate which are useful as intermediates in the synthesis of compounds of formula II, preferably 5-benzoyl-2,3-dihydro-1H-pyrrolizine-1-carboxylic acid, which are therapeutically useful as discussed hereinbefore.

EXAMPLES

The following preparations and examples are given to enable those skilled in the art to more clearly understand and to practice the present invention. They should not be considered as limiting the scope of the invention, but merely as being illustrative and representative thereof.

Preparation 1 Aroylpyrroles

2-Benzoylpyrrole

To a solution of N,N-dimethylbenzamide (48.0 g, 0.32 mol) in 1,2-dichloroethane (500 mL) was added oxalyl chloride (48.0 g, 0.38 mol). The reaction mixture was stirred for 24 hours at room temperature. To the reaction mixture was then added pyrrole (22.0 g, 0.33 mol). The reaction mixture was again stirred for 24 hours at room temperature. Aqueous sodium acetate (20%, 200 mL) was added to the reaction mixture and vigorous stirring was continued for 24 hours at room temperature. The organic layer was filtered through a silica gel column and concentrated under reduced pressure to yield 2-benzoylpyrrole which was used without further purification. Yield 43.0 g (80%).

Preparation of Other Aroylpyrroles

By following the procedure of part A above and substituting for N,N-dimethylbenzamide the following compounds:
N,N-dimethyl-4-methoxybenzamide,
N,N-dimethyl-4-methylthiobenzamide,
N,N-dimethyl-2,4-dichlorobenzamide, or
N,N-dimethyl-3-methylbenzamide; there are obtained the following compounds:
2-(4-methoxybenzoyl)pyrrole,
2-(4-methylthiobenzoyl)pyrrole,
2-(2,4-dichlorobenzoyl)pyrrole, and
2-(3-methylbenzoyl)pyrrole,

Preparation of Additional Aroylpyrroles

By following the procedures of U.S. Pat. Nos. 4,089,969 and 4,353,829 and substituting other N,N-dialkylarylamides or arylmorpholines for N,N-dimethylbenzamide, additional 2-aroylpyrroles may be obtained.

EXAMPLES 1

Preparation of Compounds of Formula III where X is Alkoxycarbonyl

A Compound of Formula III where X is Alkoxycarbonyl, Triethyl (5-benzoylpyrrol-2-yl) methanetricarboxylate To an 80° C. solution of manganese(II) acetate tetrahydrate (6.13 g, 25 mmol) in acetic acid (50 mL) was added potassium permanganate (0.99 g, 6.3 mmol). The mixture was stirred at 80° C. for 10 minutes. To the mixture was added acetic anhydride (9.68 g, 75 mmol). The mixture was stirred at 80° C. for 30 minutes and was then cooled to 60° C. To the reaction mixture was then added sodium acetate (1.64 g, 20 mmol), 2-benzoylpyrrole (1.71 g, 10 mmol) and triethyl methanetrioarboxylate (2.55 g, 11 mmol). The reaction mixture was stirred at 60° C. for 24 hours. The mixture was poured into water (50 mL) and extracted with toluene (3×25 mL). The combined toluene extracts were concentrated under reduced pressure. The residue was purified by flash chromatography on silica eluting with hexane/ethyl acetate (90:10) to provide 3.5 g (86%) of triethyl (5-benzoylpyrrol-2-yl) methane-tricarboxylate which crystallized upon standing. The product can be further purified by recrystallization from methanol. Triethyl (5-benzoylpyrrol-2-yl)-methanetricarboxylate has the following properties: m.p. 72.5–74 C; For $C_{21}H_{23}NO_7$ Calc.: C, 62.83; H, 5.77; N, 3.49; Found: C, 61.69; H, 5.62; N, 3.30

Other Compounds of Formula III where X is Alkoxycarbonyl

By following the procedure of part A above and substituting other aroyl pyrroles for 2-benzoylpyrrole, there are obtained the corresponding triethyl (5-aroylpyrrol-2-yl) methanetricarboxylate.

Additional Compounds of Formula III where X is Alkoxycarbonyl

By following the procedures of parts A and B above and substituting other trialkyl methanetricarboxylates for triethyl methanetricarboxylate, there are obtained the corresponding trialkyl (5-aroylpyrrol-2-yl)-methanetricarboxylates.

EXAMPLE 2

Preparation of Compounds of Formula III where X is Acyloxy

A Compound of Formula III where X is Acyloxy, Diethyl (5-Benzoylpyrrol-2-yl)acetoxymethane-dicarboxylate A mixture of 2-benzoylpyrrole (855 mg, 5 mmol), diethyl malonate (800 mg, 5 mmol), manganese(III) acetate dihydrate (4560 mg, 15 mmol) and sodium acetate (820 mg, 10 mmol) in acetic acid (30 mL) was stirred at 70° C. under a nitrogen atmosphere. The reaction mixture was diluted with diethyl ether and filtered. The filtrate was washed with 10% aqueous sodium hydroxide and saturated aqueous sodium chloride, dried ($Na_2SO_4$), and concentrated under reduced pressure. The residue was purified by column chromatography on silica eluting with hexane/ethyl acetate (70:30) to provide 1.00 g (57%) of diethyl (5-benzoylpyrrol-2-yl)acetoxy-methanedicarboxylate.

Additional Compounds of Formula III where X is Aoyloxy

By following the procedure of part A above and substituting other dialkyl malonates for diethyl malonate, there are obtained the corresponding dialkyl (5-benzoylpyrrol-2-yl)acetoxymethanedicarboxylates.

Additional Compounds of Formula III where X is Acyloxy

By following the procedures of parts A and B above and substituting other alkanoic acids for acetic acid, there are obtained the corresponding dialkyl (5-benzoylpyrrol-2-yl) acyloxymethanedicarboxylates.

Additional Compounds of Formula III where X is Acyloxy

By following the procedures of parts A, B and C above and substituting other aroyl pyrroles for 2-benzoylpyrrole, there are obtained the corresponding dialkyl (5-aroylpyrrol-2-yl)acyloxymethane-dicarboxylates.

EXAMPLE 3

Alternative Preparation of Compounds of Formula III where X is Acyloxy

A Compound of Formula III where X is Acetoxy, Diethyl (5-Benzoylpyrrol-2-yl) acetoxymethanedicarboxylate A mixture of 2-benzoylpyrrole (855 mg, 5 mmol), diethyl chloromalonate (973 mg, 5 mmol) and manganese(III) acetate dihydrate (4560 mg, 15 mmol) in acetic acid (30 mL) was stirred at 80° C. for four hours. The reaction was cooled to room temperature, diluted with diethyl ether and filtered. The filtrate was washed with 10% aqueous sodium hydroxide and saturated aqueous sodium chloride, dried ($Na_2SO_4$), and concentrated under reduced pressure. The residue was purified by column chromatography on silica (70–30, hexanes-ethyl acetate) to provide 1.46 g (75%) of diethyl (5-benzoylpyrrol-2-yl)acetoxymethane-dicarboxylate.

Additional Compounds of Formula III where X is Acyloxy

By following the procedure of part A above and substituting other dialkyl halomalonates for diethyl bromomalonate, there are obtained the corresponding dialkyl (5-benzoylpyrrol-2-yl)acetoxymethane-dicarboxylates.

Additional Compounds of Formula III where X is Acyloxy

By following the procedures of parts A and B above and substituting other alkanoic acids for acetic acid, there are obtained the corresponding dialkyl (5-benzoylpyrrol-2-yl) acyloxymethanedicarboxylates.

Additional Compounds of Formula III where X is Acyloxy

By following the procedures of parts A, B, and C above and substituting other aroyl pyrroles for 2-benzoylpyrrole, there are obtained the corresponding dialkyl (5-aroylpyrrol-2-yl)acyloxymethane-dicarboxylate.

EXAMPLE 4

Preparation of Compounds of Formula III where X is Hydrogen

Compound of Formula III where X is Hydrogen, Diethyl (5-Bonzoylpyrrol-2-yl)metthanedicarboxylate To a solution of 2-benzoylpyrrole (171mg, 1 mmol) and diethyl bromomalonate (1185 mg, 5 mmol) in benzene (20 mL) was added triethylborane (1.0 M in hexane, 5 mL, 5 mmol). The reaction mixture was stirred for 1 hour in an open vessel. Additional triethylborane (1 mL, 1 mmol) was added and the reaction was stirred for an additional hour. The mixture was poured into water and extracted with diethyl ether. The ethereal extract was washed with saturated aqueous sodium chloride, dried ($Na_2SO_4$), and concentrated. The residue was purified by column chromatography on silica eluting with hexane/ethyl acetate (87:13) to provide 284 mg (86%) of diethyl (5-benzoylpyrrol-2-yl)methanedicarboxylate.

An Alternative Preparation of Diethyl (5-Benzoylpyrrol-2-yl)methanedicarboxylate To a mixture of 2-benzoylpyrrole (428 mg, 2.5 mmol), diethyl bromomalonate (1.73 g, 7.5 mmol) and iron(II) sulfate heptahydrate (168 mg, 0.6 mmol) in dimethyl sulfoxide (20 mL) was added dropwise hydrogen peroxide (30%, 3.82 mL, 37.5 mmol). The reaction mixture was poured into water and extracted with methylene chloride. The methylene chloride extract was washed with saturated aqueous sodium bicarbonate and concentrated under reduced pressure. The residue was chromatographed on silica eluting with hexane/ethyl acetate (87:13) to provide 480 mg (58%) of diethyl (5-benzoylpyrrol-2-yl) methanedicarboxylate.

Additional Compounds of Formula III where X is Hydrogen

By following the procedure of part A or B above and substituting other dialkyl halomalonates for diethyl bromomalonate, there are obtained the corresponding dialkyl (5-benzoylpyrrol-2-yl)-methanedicarboxylates.

Additional Compounds of Formula III where X is Hydrogen

By following the procedures of parts A, B and C above and substituting other aroyl pyrroles for 2-benzoylpyrrole, there are obtained the corresponding dialkyl (5-aroylpyrrol-2-yl)methanedicarboxylate.

EXAMPLE 5

Preparation of Compounds of Formula III where X is Hydrogen from compounds of Formula III where X is Acyloxy

A Compound of Formula III where X is Hydrogen, Diethyl (5-BenzoylpYrrol-2-yl)methanedicarboxylate To a solution of diethyl (5-benzoylpyrrol-2-yl)-acetoxymethanedicarboxylate (142 mg, 0.367 mmol) and triethylsilane (102 mg, 0.440 mmol) in methylene chloride (10 mL) was added trifluoroacetic acid (84 mg, 0.734 mmol). The reaction mixture was stirred at 40° C. for 24 hours. Additional triethyl silane (51 mg, 0.220 mmol) and trifluoroacetic acid (84 mg, 0.734 mmol) was added. The reaction mixture was stirred at 40° C. for an additional 24 hours. The mixture was cooled to room temperature, washed with cold 10% aqueous sodium hydroxide and saturated aqueous sodium chloride, and concentrated under reduced pressure. The residue was purified by column chromatography on silica eluting with hexane/ethyl acetate (87:13) to provide 60 mg (50%) of diethyl (5-benzoylpyrrol-2-yl)methane-dicarboxylate.

Other Compounds of Formula III where X is Hydrogen

By following the procedure of part A above and substituting other dialkyl (5-aroylpyrrol-2-yl)-acyloxymethanedicarboxylates for diethyl (5-benzoyl-pyrrol-2-yl)acetoxymethanedicarboxylate, there are obtained the corresponding dialkyl (5-aroylpyrrol-2-yl)methane-dicarboxylates.

EXAMPLE 6

Preparation of Compounds of Formula I from compounds of Formula III where X is Alkoxycarbonyl

A Compound of Formula I, Diethyl 5-Benzoyl-2,3-dihydro-1H-pyrrolizine-1,1-dicarboxylate A mixture of triethyl (5-benzoylpyrrol-2-yl)-methanetricarboxylate (2.00 g, 5 mmol), tetra-butylammonium bromide (1.61 g, 5 mmol) and potassium carbonate (19.0 g, 250 mmol) in 1,2-dichloroethane (100 mL) was refluxed for 2 days. The mixture was cooled to room temperature and filtered. The filter cake was washed with methylene chloride. The filtrate and methylene chloride wash solution were combined and concentrated under reduced pressure. The residue was dissolved in diethyl ether, washed with water, dried, and concentrated. The crude product was purified by flash chromatography on flash silica eluting with hexane/ethyl acetate (90:10) to provide 1.42 g (80%) of diethyl 5-benzoyl-2,3-dihydro-1H-pyrrolizine-1,1-dicarboxylate. The IR and NMR spectral properties were identical to those of the authentic sample.

Other Compounds of Formula I

By following the procedure of part A above and substituting other trialkyl (5-aroylpyrrol-2-yl)-methanetricarboxylates for triethyl (5-benzoylpyrrol-2-yl) methanetricarboxylate, there are obtained the corresponding dialkyl 5-aroyl-2,3-dihydro-1H-pyrrolizine-1,1-dicarboxylates.

EXAMPLE 7

Preparation of Compounds of Formula I from Compounds of Formual III where X is Hydrogen A compound of Formula I, Diethyl 5-Bensoyl-2,3dihydro-1H-pyrrolizine-1,1-dicarboxylate A mixture of diethyl (5-benzoylpyrrol-2- yl) methanedicarboxylate (130 mg, 0.4 mmol), tetrabutylammonium bromide (2.76 g, 20.0 mmol) in 1,2-dichloroethane (16 mL) was refluxed for 24 hours. The reaction mixture was cooled to room temperature and filtered. The filtrate was concentrated under reduced pressure and diluted with diethyl ether. The solution was washed with water, dried (Na2SO4), and concetrated under reduced pressure. The residue was purified by chromatography on silica eluting with hexanes/ethyl acetate (90:10) to provide 95 mg (67%) of diethyl 5-benzoyl-2,3-dihydro-1H-pyrrolizine-1,1-dicarboxylate.

Other Compounds of Formula I

By following the procedure of part A above and substituting other dialkyl (5-aroylpyrrol-2-yl)methanedicarboxylates for diethyl (5-benzoylpyrrol-2-yl)-methanedicarboxylate, there are obtained the corresponding dialkyl 5-aroyl-2,3-dihydro-1H-pyrrolizine-1,1-dicarboxylates.

EXAMPLE 8

Preparation of Compounds of Formula II

A Compound of Formula II, 5-Benzoyl-z,3-dihydro-1H- pyrrolizine-1-carboxylic acid A mixture of diethyl 5-benzoyl-2,3-dihydro-1H-pyrrolizine-1,1-dicarboxylate (600 mg, 1.69 mmol) in diethyl ether and 20% aqueous sodium hydroxide (10 mL) was refluxed with vigorous stirring for 24 hours. The aqueous layer was washed with ether (20 mL), and acidified with concentrated hydrochloric acid. The aqueous layer was washed with ethyl acetate (3×20 mL). The ethyl acetate extracts were combined and warmed at 70° C. for 4 hours. The ethyl acetate solution was concentrated under reduced pressure to yield 400 mg (93%) of 5-benzoyl-2,3-dihydro-1H-pyrrolizine-1-carboxylic acid as a pure solid.

Other Compounds of Formula II

By following the procedure of part A above and substituting other dialkyl 5-aroyl-2,3-dihydro-1H-pyrrolizine-1,1-dicarboxylate for diethyl 5-benzoyl-2,3-dihydro-1H-pyrrolizine-1,1-dicarboxylate, there are obtained the corresponding 5-aroyl-2,3-dihydro-1H-pyrrolizine-1-carboxylic acids.

EXAMPLE 9

Preparation of Salts of Compounds of Formula II

Preparation of the Tromethamine salt of a Compound of Formula II

To a warm solution of 5-benzoyl-2,3-dihydro-1H-pyrrolizine-1-carboxylic acid (200 mg, 0.78 mmol) in 15 mL of benzene was added tromethamine (60 mg, 0.49 mmol). The reaction mixture was cooled and filtered. The precipitate was washed with ether and dried to yield the tromethamine salt of 5-benzoyl-2,3-dihydro-1H-pyrrolizine-l-carboxylic acid.

Other salts of Compounds of Formula II

In similar manner, the compounds of formula II can be converted to their corresponding pharmaceutically acceptable salts by treatment with the appropriate amine, for example, diethylamine, ethanolamine, piperidine, isopropylamine, choline, caffeine and the like.

We claim:

1. A process for producing a compound of formula III,

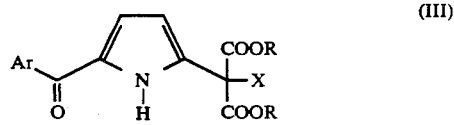

(III)

in which X is hydrogen, each R is independently lower alkyl and Ar is aryl,
   which comprises treating an aroyl pyrrole with a dialkyl halomalonate and an alkyl radical in an aprotic solvent.

2. The process of claim 1 wherein Ar is selected from 4-(R"W)-phenyls.

3. A process of claim 1 wherein Ar is phenyl and R is ethyl.

4. The process of claim 1 wherein the dialkyl halomalonate is diethyl bromomalonate and the alkyl radical is methyl.

5. The process of claim 4 wherein the methyl radical is produced from the reaction of ferrous sulfate and hydrogen peroxide in dimethyl sulfoxide.

6. The process of claim 1 wherein the dialkyl halomalonate is diethyl bromomalonate and the alkyl radical is produced from the reaction of a trialkylborane and oxygen in the aprotic solvent.

7. A process for producing a compound of formula I,

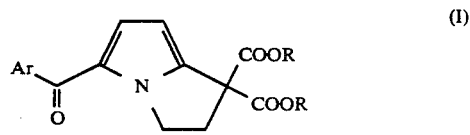

(I)

in which each R is independently lower alkyl and Ar is aryl, which comprises heating a compound of formula III,

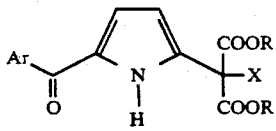
(III)

in which X is alkoxycarbonyl or hydrogen, and R and Ar are as defined above, with bromide or iodide ion and a base in a 1,2-dihaloalkane.

8. The process of claim 7 wherein Ar is selected from 4-(R″W)-phenyls.

9. The process of claim 7 wherein Ar is phenyl and R is ethyl.

10. The process of claim 7 wherein the bromide ion is derived from tetrabutylammonium bromide and the 1,2-dihaloalkane is 1,2-dichloroethane.

11. The process of claim 7 wherein the iodide ion is derived from tetrabutylammonium iodide and the 1,2-dihaloalkane is 1,2-dichloroethane.

12. A compound of formula III,

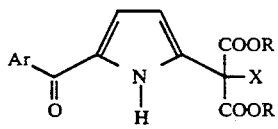
(III)

in which
X is alkoxycarbonyl, acyloxy or hydrogen, each R is independently lower alkyl, and Ar is aryl.

13. The compound of claim 12 wherein Ar is selected from 4-(R″W)-phenyls and X is alkoxycarboryl.

14. The compound of claim 12 wherein Ar is selected from 4-(R″W)-phenyls and X is acyloxy.

15. The compound of claim 12 wherein Ar is selected from 4-(R″W)-phenyls and X is hydrogen.

16. The compound of claim 13 wherein Ar is phenyl and R is ethyl.

17. The compound of claim 14 wherein Ar is phenyl and R is ethyl.

18. The compound of claim 15 wherein Ar is phenyl and R is ethyl.

* * * * *